US012575957B2

(12) United States Patent
Winnett

(10) Patent No.: US 12,575,957 B2
(45) Date of Patent: Mar. 17, 2026

(54) BACK SUPPORT DEVICE

(71) Applicant: Gregory W. Winnett, Charleroi, PA (US)

(72) Inventor: Gregory W. Winnett, Charleroi, PA (US)

( * ) Notice: Subject to any disclaimer, the term of this patent is extended or adjusted under 35 U.S.C. 154(b) by 0 days.

(21) Appl. No.: 18/824,036

(22) Filed: Sep. 4, 2024

(65) Prior Publication Data

US 2026/0060831 A1 Mar. 5, 2026

(51) Int. Cl.
*A61F 5/02* (2006.01)

(52) U.S. Cl.
CPC .................................... *A61F 5/028* (2013.01)

(58) Field of Classification Search
CPC .. A61F 5/02; A61F 5/022; A61F 5/024; A61F 5/026; A61F 5/028; A61F 13/14; A61F 13/146; A61F 13/148; A61H 3/00; A61H 3/008
See application file for complete search history.

(56) References Cited

U.S. PATENT DOCUMENTS

| | | | | |
|---|---|---|---|---|
| 5,951,591 A * | 9/1999 | Roberts | | A61F 5/02 |
| | | | | 606/241 |
| 6,766,532 B1 * | 7/2004 | Cabana | | A61F 5/028 |
| | | | | 2/310 |
| 7,553,266 B2 * | 6/2009 | Abdoli-Eramaki | | A63B 21/00181 |
| | | | | 602/19 |
| 7,833,182 B2 * | 11/2010 | Hughes | | A61F 5/026 |
| | | | | 602/5 |
| 8,556,840 B2 * | 10/2013 | Burke | | A61F 5/026 |
| | | | | 602/19 |
| D1,039,267 S * | 8/2024 | Lin | | D3/228 |
| 2022/0071794 A1 * | 3/2022 | Bartenbach | | A61F 5/026 |
| 2023/0149199 A1 * | 5/2023 | Perez | | A61F 5/028 |
| | | | | 602/19 |

* cited by examiner

*Primary Examiner* — Kari K Rodriquez
(74) *Attorney, Agent, or Firm* — Acker Wood IP Law, LLC; Gwen R. Acker Wood

(57) ABSTRACT

The invention provides an adjustable back support device configured to fit a user's height and waist size comprised of a harness, an articulating support structure, and an elastic support strap attached to the articulating support structure. The device provides spinal support, alignment, and back muscle assistance to a user when external forces are applied to the user's upper body and back muscles. The device fits over the shoulders and around the waist of a user and is supported vertically by the harness and laterally by a waist support belt. The elastic support strap provides resistance to the back muscles when a user bends from the waist. Resistance of the elastic support strap may be increased or decreased by an elastic strap tensioner assembly which adjusts resistance of the elastic support strap via a tensioner pin which contains a plurality of lockable positions for varying resistance of the elastic support strap.

20 Claims, 6 Drawing Sheets

10

15

17

13

12

18

21

21'

13'

16

26

26'

53

50

24

53

19

28

28

22

14

BACK SUPPORT DEVICE

FIELD OF THE INVENTION

This invention relates to the field of human health, fitness, and physical wellness. More specifically, the invention comprises a wearable device which supports, aligns, and assists the muscles of the back.

BACKGROUND OF THE INVENTION

There are many known back support devices available on the market. Most of these are of the "support type" that are made from elastic material with end structures of both straps and buckle arrangements or hook and loop fasteners. These types of back support devices are often referred to as support belts. They function by creating support in a radial position around the torso by applying pressure to the waist and lower back areas by using compression of the surrounding tissues to provide a feeling of support for the back muscles. Some variations of this type of support belt use shoulder straps to vertically support the belt and to help secure the position of the support belt in the lumbar region of the torso. These support belts provide compression support only and do not provide assistance, i.e., supplemental force, to the back muscles themselves.

Rehabilitation after spinal injury may include the use of lumbar support using an elastic type support belt. The effectiveness of radial compression supplied by such lumbar support belts is limited due to the lack of force, or pressure, acting directly and focused on a specific area of the spine. Further, lumbar support belts have little effect on back muscles. There exists a need, therefore, for an advanced back support device that overcomes the shortcomings of back support devices currently available.

SUMMARY OF THE INVENTION

The present invention fulfills this need by providing an adjustable back support device which is configured to replicate the shoulders, spine, and hips of the skeletal structure of a user's body and to move with the user's body so that the shoulders, spine and hips are supported and properly aligned and the user's back muscles are assisted when external forces are applied to the user's upper body which result in exertion of the back muscles. The adjustable back support device comprises an adjustable support structure and an elastic support strap that is attached to the support structure and positioned at the center of a user's back and aligned with the spinal column of the user. The elastic member provides resistance force to counteract forces acting upon a user's upper body. The support structure includes a hinge that, when properly adjusted according to the height a user, is positioned atop the tailbone, i.e., (coccyx).

In particular, in an aspect of the invention, there is provided an adjustable back support device comprised of a shoulder support harness comprised of a first side, a second side, and a middle portion. The shoulder support harness is configured to fit atop a user's shoulders, wherein the first and second sides are positioned over a user's chest and the middle portion is positioned on the user's back.

The adjustable back support device further comprises an adjustable support structure comprised of an upper support beam, a main support beam, and a lower support beam. The upper support beam is contiguous with one end of the main support beam, the lower support beam is mounted atop and attached to an opposite end of the main support beam and oriented perpendicularly thereto, and the shoulder support harness is mounted atop and attached to the upper support beam.

The adjustable back support device also comprises an adjustable waist support belt mounted atop and attached to the lower support beam; a pair of adjustable harness straps, one harness strap attached at one end to the first side of the shoulder support harness and the other harness strap attached at one end to the second side of the shoulder support harness. Each of the harness straps at its opposite end is configured to attach to the waist support belt.

The adjustable back support device further comprises an adjustable elastic support strap having a first end and a second end. The first end is attached to the middle portion of the shoulder support harness and the second end secured to the waist support belt.

The adjustable back support device further comprises an elastic strap tensioner assembly comprised of a tensioner base, a tensioner arm, a tensioner arm roller attached perpendicularly to the tensioner arm and configured to roll under the elastic support strap as the tensioner arm is raised upwardly, a tensioner arm rotatable pivot, a tensioner arm pin, and a tensioner indicator scale. The elastic strap tensioner assembly is configured to provide a plurality of levels of tension in the elastic support strap as the tensioner arm with attached tensioner arm roller is raised in an upwardly direction. As the tensioner arm is raised upwardly, the tensioner arm pin moves upwardly to indicate on the tensioner indicator scale the level of tension on the elastic support strap. The tensioner arm pin that is contiguous with the tensioner pivot is used to adjust the position of the tensioner arm.

In another aspect of the invention, there is provided a method for providing spinal support, alignment, and back muscle assistance when external forces are applied to the upper body of a user using the adjustable back support device described above. The method comprises positioning the shoulder support harness with attached upper support beam and main support beam atop the shoulders of the user; positioning the waist support belt with attached lower support beam around the user's hips; positioning the upper support beam and the main support beam centrally on the user's back so that they are aligned with the user's spinal column; adjusting the length of the upper support beam and the main support beam to conform to the height of the user by positioning the main support beam hinge atop the tailbone area of the user and inserting the upper support beam into the height adjustment assembly of the main support beam to achieve this positioning, wherein the user is able to determine the degree of insertion of the upper beam support into the main support beam by viewing the reference scale shown on the upper support beam; securing the shoulder support harness on the user by securing the pair of harness straps onto the waist support belt; adjusting tension of the elastic support strap by rotating the tensioner arm of the elastic support strap tensioner assembly upwardly and placing the tensioner arm into one of a plurality of lockable positions on the tensioner base; and locking the tensioner arm into the one of the plurality of lockable positions as indicated by the location of the tensioner arm pin so that the tensioner arm roller is stationary on the elastic support strap and maintains a desired degree of tension in the elastic support strap, wherein when a user bends at the waist and external forces are applied to the user's upper body to cause exertion of the back muscles, the main support beam hinge allows for articulation of the main support beam so that spinal support, spinal alignment, and back muscle assistance is provided to the user.

BRIEF DESCRIPTION OF THE DRAWINGS

A clear understanding of the key features of the invention summarized above may be had by reference to the appended drawings, which illustrate the invention, although it will be understood that such drawings depict preferred embodiments of the invention and, therefore, are not to be considered as limiting its scope with regard to other embodiments which the invention is capable of contemplating. Accordingly.

DETAILED DESCRIPTION OF THE INVENTION

Figure 1:
FIG. 1 is a rear perspective view of the adjustable back support device.
Figures 2, 3:
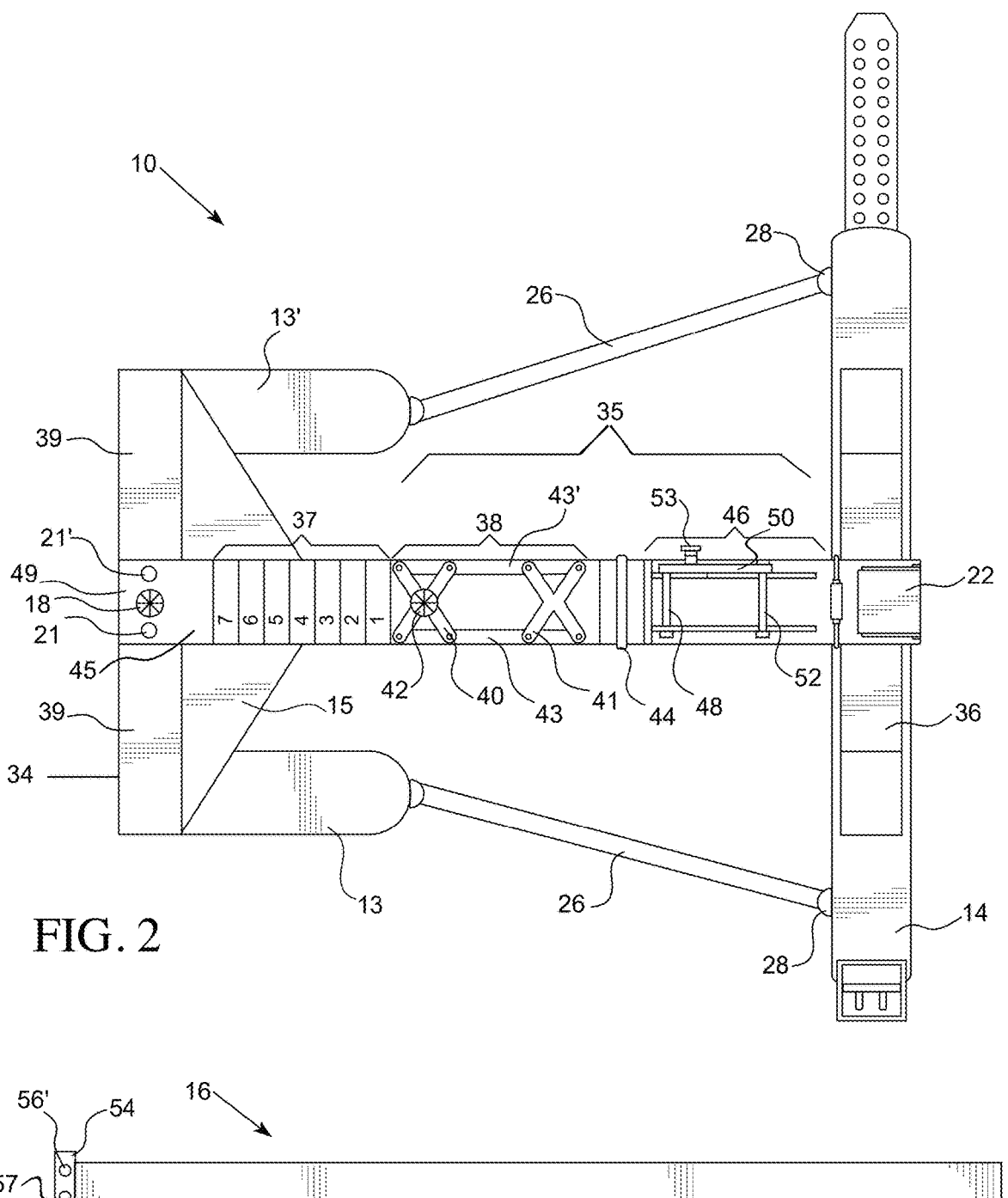
FIG. 2 is a top plan view of the adjustable back support device minus the shoulder support harness and the elastic support strap.
FIG. 3 is a top plan view of the elastic support strap.

Referring now to the figures, as shown in FIGS. 1-3, in an embodiment of the invention there is provided an adjustable back support device 10 having a shoulder support harness 12 comprised of a first side 13, a second side 13', and a middle portion 15. The shoulder support harness 12 is configured to fit over a user's head and rest atop a user's shoulders with the first and second sides 13, 13' positioned on the user's chest and the middle portion 15 positioned on the user's back. A first harness attachment strap 26 is attached at one end to the first side 13 of the shoulder support harness 12 and a second harness attachment strap 26' is attached at one end to second side 13' of the shoulder support harness 12. The other ends of the first and second harness attachment straps 26, 26' each attach to a waist support belt 14 with an attachment means 28. The harness attachment straps 26, 26' may be made from any suitable material including, but not limited to, nylon. Any suitable attachment means may be used to attach the harness attachment straps 26, 26' to the waist support belt 14 including, but not limited to, slip buckles, cam buckles or clasp and loop-type fasteners. In an embodiment, the first and second harness attachment straps 26, 26' each are attached to the waist support belt 14 with a clasp and loop fastener.

As shown in FIG. 2, the back support device 10 further comprises a main support beam 35, an upper support beam 34, and a lower support beam 36. The upper support beam 34 is a T-shaped structure having an upper portion 49 comprised of two lateral arms 39 and a central elongated arm 45. The elongated arm 45 of the upper support beam 34 and the main support beam 35 are contiguous and axial to one another. The main support beam 35 and the lower support beam 36 are contiguous to one another, with the lower support beam 36 oriented perpendicular to the main support beam 35. The main support beam 35 is configured to be aligned with a user's spinal column and serves as a mounting base for the upper support beam 34 and the lower support beam 36. The upper portion 49 of the upper support beam 34 is configured to serve as a mounting base for the shoulder support harness 12 which is attached thereto and the lower support beam 36 is configured to serve as a mounting base for the waist support belt 14 which is attached thereto. Between the two lateral arms 39 of the upper support beam 34 there is a pair of strap attachment pins 21, 21' with a strap attachment knob 18 located therebetween.

The upper support beam 34, the main support beam 35, and the lower support beam 36 may be manufactured from any suitable solid material including, but not limited to, aluminum, steel, rigid plastics or laminate fiber materials.

Any suitable attachment means may be used to attach the shoulder support harness 12 to the upper portion 49 of the upper support beam 34 and the waist support belt 14 to the lower support beam 36 including, but not limited to, screws, glue-like substances, and hook and loop-type fasteners.

The invention further comprises an elastic support strap 16 having a first end 17 and a second end 19 (shown in FIGS. 1 and 3). The first end 17 of the elastic support strap 16 has an elastic support strap attachment 54 having two elastic support strap guide holes 56, 56' located on opposite ends of the elastic support strap attachment 54 and an elastic support strap attachment center hole 57 (best shown in FIG. 3). The first end 17 of the elastic support strap 16 is attached to the upper portion 49 of the upper support beam 34 by inserting each of the elastic support strap guide holes 56, 56' into a corresponding elastic support strap attachment pin 21, 21' and securing the elastic support strap 16 to the upper support beam 34 by tightening the elastic support strap knob 18 into the elastic support strap attachment center hole 57. The second end 19 of the elastic support strap 16 is attached and secured to the waist support belt 14 by inserting the second end 19 into a cam buckle 22 having a cam buckle retainer 24. The shape of the elastic support strap 16 may vary from round rope-type straps to flat rubber band-like shapes. Any suitable flexible material may be used to manufacture the elastic support strap 16 including, but not limited to, rubber, elastics, buna, or neoprene.

Figure 4:
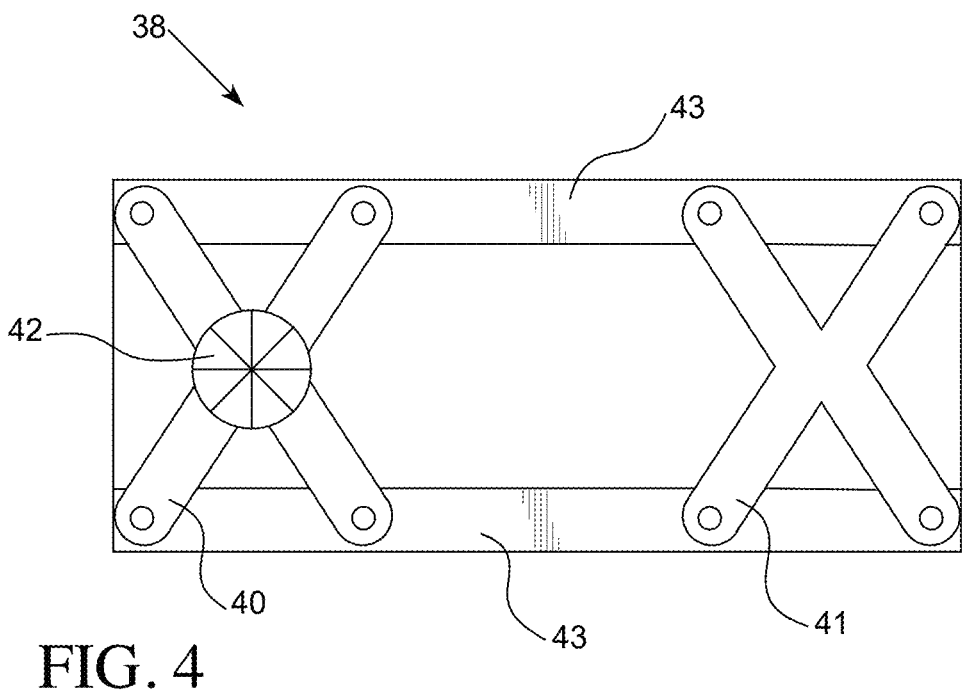
FIG. 4 is a top plan view of the height adjustment assembly.
Figure 5:
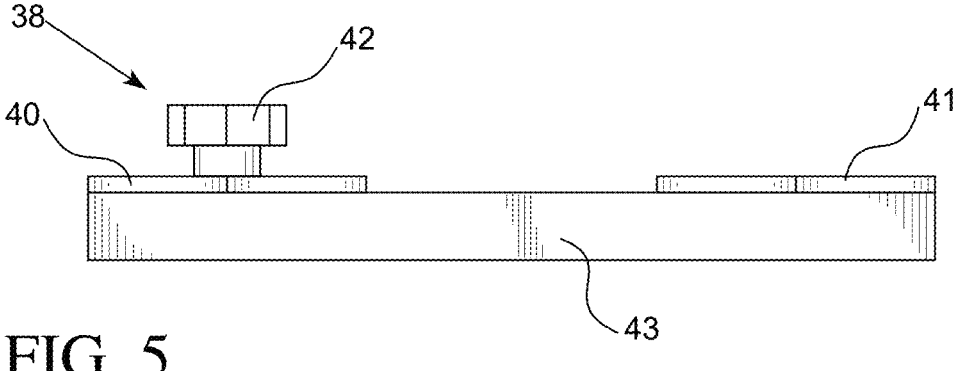
FIG. 5 is a side plan view of the height adjustment assembly.

Referring now to FIGS. 4-5, the main support beam 35 includes a height adjustment assembly 38 comprised of a first height adjustment strap 40 and a second height adjustment strap 41. The height adjustment straps 40, 41 are mounted atop and affixed to two parallel height assembly guides 43. The first height adjustment strap 40 has a rotatable height adjustment knob 42 at its center.

The central elongated arm 45 of the upper support beam 34 is configured to insert into the height adjustment assembly 38 of the main support beam 35 so that the total length of the upper support beam 34 and the main support beam 35 can be adjusted according to a user's height. The central elongated arm 45 of the upper support beam 35 is secured within the height adjustment assembly 38 by tightening the height adjustment knob 42 therein. In addition, the elongated arm 45 of the upper support beam 34 includes a height indicator scale 37 etched or stamped onto the surface of the elongated arm 45. The numeric indicators on the height indicator scale 37 are configured to so that a user can view the degree of insertion of the central elongated arm 45 into main support beam 35 that is desired for the user's height.

The length of the adjustable back support device 10 is determined by the amount of insertion of the upper support beam 34 into the main support beam 35 and accommodates users of average height. However, the use of a longer upper support beam 34 may be used in the invention to accommodate taller users, i.e., over six feet tall.

The main support beam 35 further comprises a main support beam hinge 44 located adjacent to the second height adjustment strap 41. The main support beam hinge 44 is configured to allow articulation of the main support beam 35 when a user bends from the waist which applies a force to the upper support beam 34 and the lower support beam 36.

Figure 6:
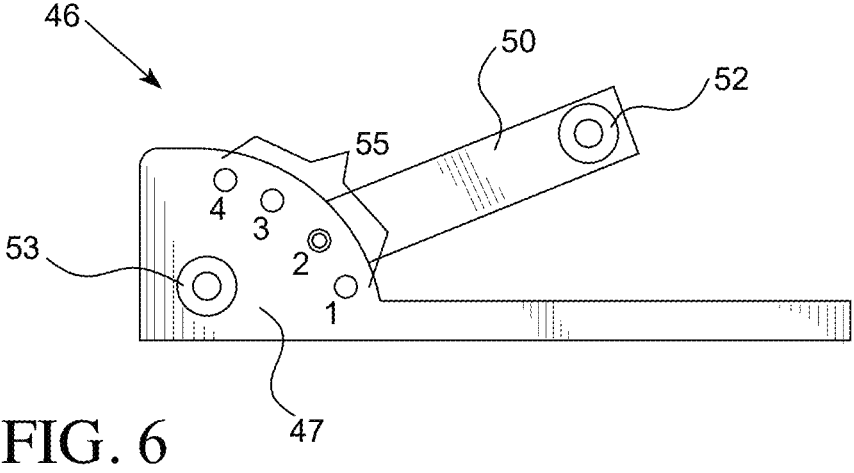
FIG. 6 is a side plan view of the elastic strap tensioner assembly.
Figure 7:
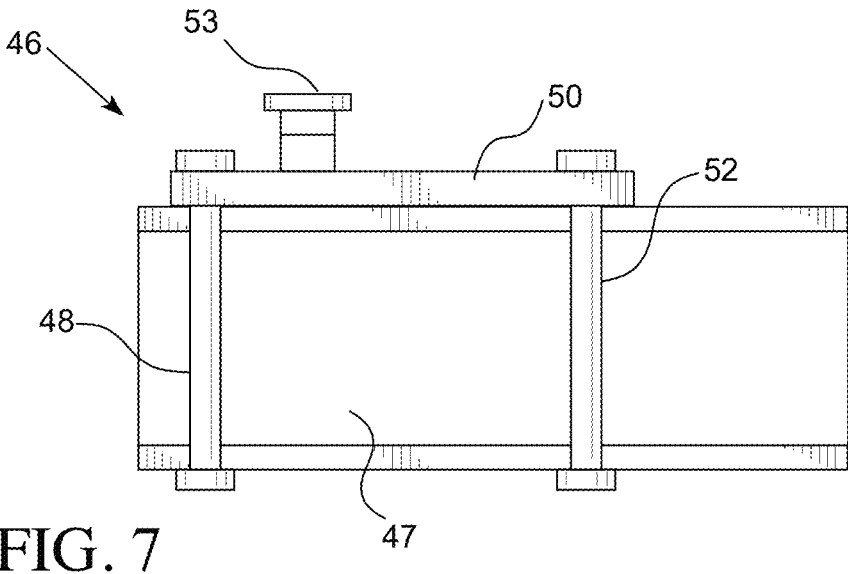
FIG. 7 is a top plan view of the elastic strap tensioner assembly.

Referring now to FIGS. 6 and 7, the main support beam 35 also comprises an elastic support strap tensioner assembly 46 comprised of a tensioner base 47, a rotatable tensioner arm pivot 48, a tensioner arm 50 attached to and oriented perpendicularly to the rotatable tensioner arm pivot 48, a tensioner arm roller 52 attached to and oriented perpendicularly to the tensioner arm 50, a tensioner arm pin 53 that is contiguous with the tensioner arm pivot 48, and a tensioner indicator scale 55. The elastic strap tensioner assembly 46 is configured to increase tension, or tensile force, in the elastic support strap 16 as the tensioner arm 50 is raised in an upwardly direction and the tensioner arm roller 50 correspondingly rolls upwardly along the elastic support strap 16 causing increasing levels of tension on the elastic support strap 16. The tensioner arm 50 is raised upwardly by rotating the tensioner arm pin 48 counterclockwise. The tensioner indicator scale 55 indicates the degree of tension exerted on the elastic support strap 16. In an embodiment, the tensioner indicator scale 55 includes four levels of tension corresponding to four positions to which the tensioner arm 50 can be locked into position on the tensioner base 47, numbered 1 through 4, with position 1 being the lowest tension exerted on the elastic support strap 16 and position 4 being the highest tension exerted on the elastic support strap 16.

Figure 8:
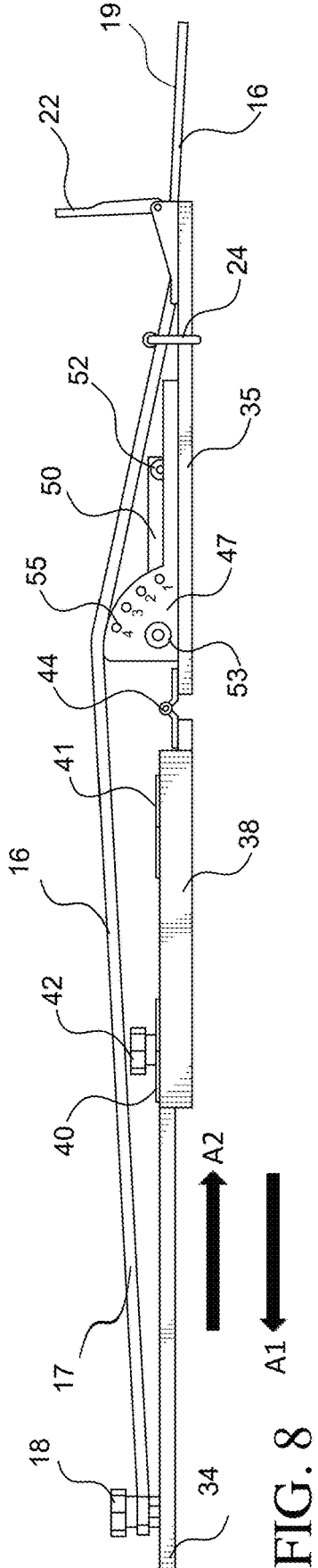
FIG. 8 is a side plan view of the adjustable back support device, minus the shoulder support harness and the waist support belt, showing the elastic support strap inserted but not secured to the cam buckle, and the tensioner arm of the elastic strap tensioner assembly locked in tension position "1"
Figure 9:
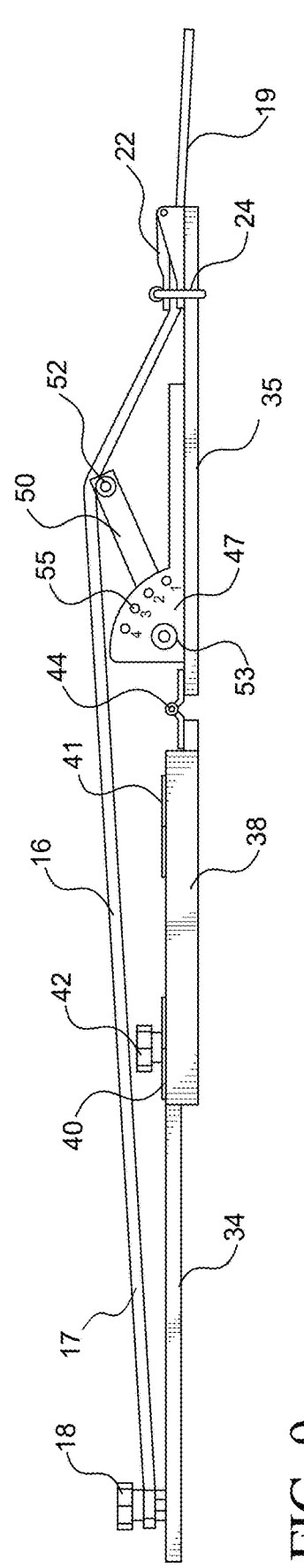
FIG. 9 is a side plan view of the adjustable back support device, minus the shoulder support harness and the waist support belt, showing the elastic support strap secured in the cam buckle by the cam buckle retainer, and the tensioner arm of the elastic strap tensioner assembly locked in tension position "2"

The adjustable back support device when in use is positioned at the center of a user's back and aligned with the spinal column. The elastic strap provides the resistance force to counteract the force acting upon the user's upper body when the user is engaged in activity that exerts force on the user's back muscles. The shoulder support harness attached to the upper support beam and main support beam is positioned atop a user's shoulder and the main support beam hinge is positioned atop the tailbone area (coccyx) of the user's body. The waist support belt with the lower support beam is placed around the user's waist and positioned so that it rests atop the user's hips. The length of the device then is adjusted according to the height of the user by sliding the upper support beam into the height adjustment assembly of the main support beam. A visual reference scale on the upper support beam may be used to view the degree of insertion of the upper support beam in the main support beam. After the length of the device is fit to the height of the user, the elastic support strap is positioned on the waist support belt by inserting the second end of the waist support belt into the cam buckle, as shown in FIG. 8. The elastic support strap is secured on the waist support belt by lowering the cam buckle retainer onto the cam buckle, as shown in FIG. 9. The length of the shoulder support harness adjustment straps are adjusted and then affixed to the waist support belt. The user then manipulates the tensioner arm pin on the elastic support strap tensioner arm assembly to adjust the position of the tensioner arm and the degree of tension exerted on the elastic support strap by the tensioner arm roller.

Figure 10:
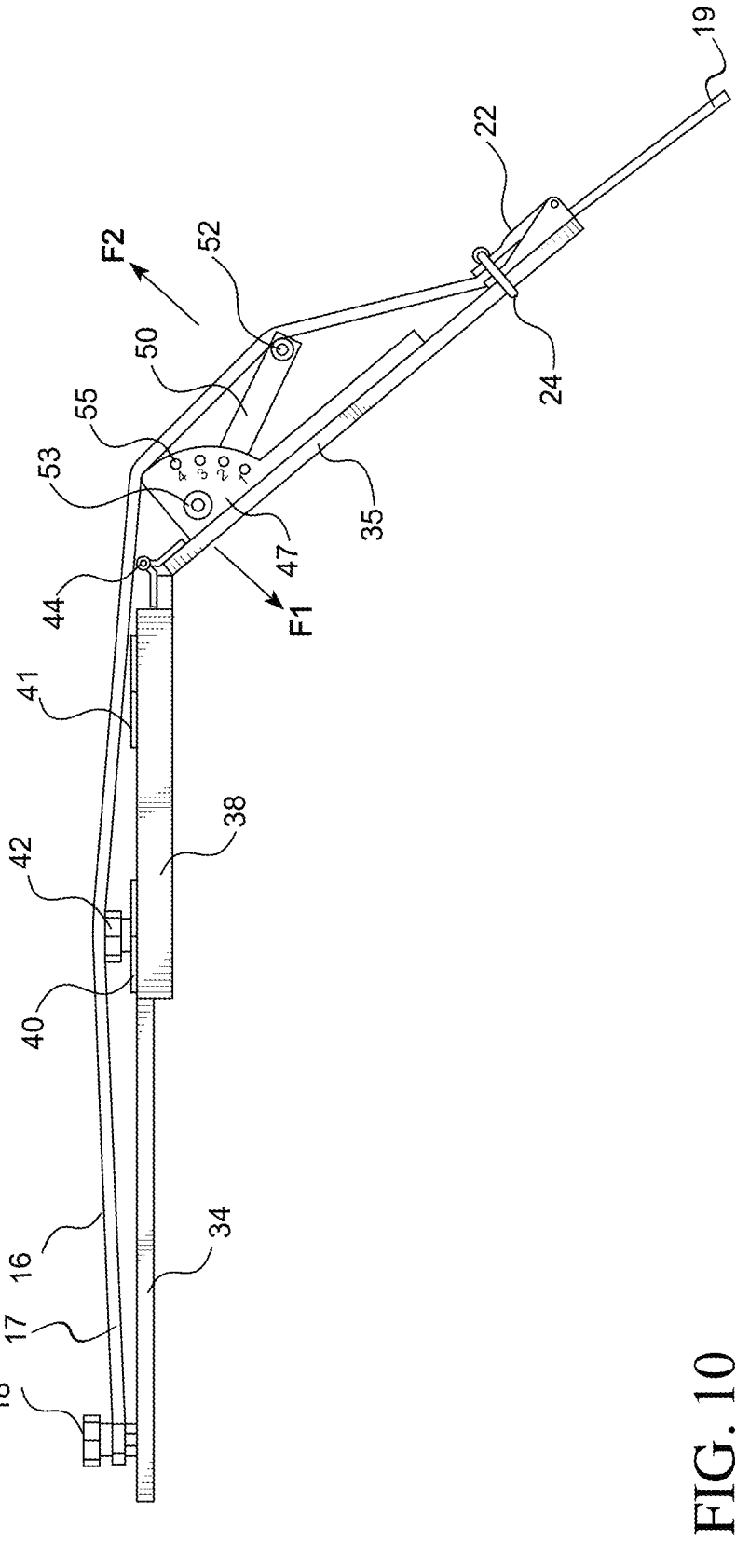
FIG. 10 is a side plan view of the adjustable back support device, minus the shoulder support harness and the waist support belt, showing the elastic support strap secured in the cam buckle by the cam buckle retainer, the tensioner arm of the elastic strap tensioner assembly locked in position "2", and the main support beam forming an angle via the articulating main support beam hinge.

During activity that may place a degree of exertion on the back muscles of a user, when the user bends from the waist, the main support beam hinge applies a direct force to the tailbone area of the user, F1, which causes an opposite reactive force on the shoulders and the hips of the user, F2 (shown in FIG. 10), which results in the user's body being pulled in a straight or inline position which assists the back muscles during the activity.

Although this invention has been described in specific detail with reference to the disclosed embodiments, it will be understood that many variations and modifications may be affected within the spirit and scope of the invention as described in the appended claims.

The invention claimed is:

1. An adjustable back support device to support, align and assist back muscles of a user when external forces are applied to the upper body of the user, comprising:

a shoulder support harness comprised of a first side, a second side, and a middle portion, said shoulder support harness configured to fit atop a user's shoulders, wherein the first and second sides are positioned on a user's chest and the middle portion is positioned on the user's back;

an adjustable support structure comprised of an upper support beam, a main support beam, and a lower support beam, wherein said upper support beam is contiguous with one end of the main support beam and the lower support beam is mounted atop and attached to an opposite end of the main support beam and oriented perpendicularly thereto, wherein said shoulder support harness is mounted atop and attached to the upper support beam;

an adjustable waist support belt mounted atop and attached to the lower support beam;

a pair of adjustable harness straps, one harness strap attached at one end to the first side of the shoulder support harness and the other harness strap attached at one end to the second side of the shoulder support harness, wherein each of the harness straps at its opposite end is configured to attach to the waist support belt;

an adjustable elastic support strap having a first end and a second end, said first end attached to the shoulder support harness and said second end secured to the waist support belt;

a height adjustment assembly configured to adjust length of the back support device; and an elastic strap tensioner assembly configured to adjust tension in the elastic support strap comprised of a tensioner base, a tensioner arm, a tensioner arm roller, a tensioner arm rotatable pivot, a tensioner arm pin which inserts into the tensioner arm pivot, and a tensioner indicator scale, wherein the elastic strap tensioner assembly is configured to provide increasing amounts of tension in the elastic support strap as the tensioner arm is raised in an upwardly direction.

2. The adjustable back support device of claim 1, wherein the upper support beam is T-shaped and comprised of a central elongated arm and two lateral arms, wherein said shoulder support harness is mounted atop and attached to the two lateral arms of the upper support beam.

3. The adjustable back support device of claim 2, wherein between the two lateral arms there is a pair of elastic support strap attachment pins and an elastic support strap knob.

4. The adjustable back support device of claim 3, wherein the first end of the elastic support strap further comprises an elastic support strap attachment comprised of an elastic support strap center hole and pair of elastic support strap attachment guide holes on either side of the elastic support strap center hole.

5. The adjustable back support device of claim 4, wherein the pair of elastic support strap attachment guide holes on the first end of the elastic support strap insert into the pair of elastic support strap attachment pins and are secured therein with the elastic support strap knob.

6. The adjustable back support device of claim 5, wherein the second end of the elastic support strap is secured to the waist support belt by sliding through a cam buckle located on the waist support belt and secured therein by a cam buckle retainer.

7. The adjustable back support device of claim 6, wherein the adjustable harness straps attaches to the waist support belt by a pair of slip buckles, a pair of cam buckles or a pair of loop-type fasteners.

8. The adjustable back support device of claim 7, wherein the elongated portion of the upper support beam has a visual reference scale shown thereon.

9. The adjustable back support device of claim 8, wherein the main support beam is comprised of a height adjustment assembly comprised of a first height adjustment strap and a second height adjustment strap, said height adjustment straps mounted atop and affixed to two parallel height assembly guides, said first height adjustment strap having a rotatable height adjustment knob thereon.

10. The adjustable back support device of claim 9, wherein the elongated arm of the upper support beam inserts into the height adjustment assembly of the main support beam to allow total length of the upper support beam and the main support beam to be increased or decreased, wherein the visual reference scale allows the user to determine degree of insertion of the elongated arm of the upper support beam into the height adjustment assembly.

11. The adjustable back support device of claim 10, wherein the elongated arm of the upper support beam is secured within the height adjustment assembly by tightening the rotatable height adjustment knob on the first height adjustment strap.

12. The adjustable back support device of claim 11, further comprising a main support beam hinge located adjacent to the second height adjustment strap, said main support beam hinge configured to allow articulation of the main support beam when the user bends from the waist.

13. The adjustable back support device of claim 12, wherein the elastic support tensioner assembly is comprised of a tensioner base, a tensioner arm, a tensioner arm roller, a tensioner arm rotatable pivot, a tensioner arm pin which inserts into the tensioner pivot, and a tensioner indicator scale, wherein the elastic strap tensioner assembly is configured to provide increasing amounts of tension in the elastic support strap as the tensioner arm is raised in an upwardly direction and locked into one of a plurality of positions.

14. The adjustable back support device of claim 13, wherein the tensioner arm pin is used to move the tensioner arm in an upwardly direction to increase tension on the elastic support strap.

15. The adjustable back support device of claim 14, wherein the tensioner arm is raised in an upwardly direction and locked into one of four positions, said four positions shown on the tensioner indicator scale as tension positions 1 through 4, wherein tension on the elastic support strap increases proportionately from position 1 through position 4, wherein position 1 provides the least tension on the elastic support strap and position 4 provides the maximum tension on the elastic support strap.

16. The adjustable back support device of claim 15, wherein the tensioner arm roller slides along the elastic support strap as the tensioner arm is rotated upwardly to increase tension in the elastic support strap or rotated downwardly to decrease tension in the elastic support strap.

17. The adjustable back support device of claim 16, wherein the upper support beam, the main support beam and the lower support beam are manufactured from rigid materials selected from aluminum, steel, plastics or laminate fiber materials.

18. The adjustable back support device of claim 17, wherein the elastic support strap is manufactured from flexible materials selected from rubber, elastic, buna, neoprene, or any other flexible material.

19. The adjustable back support device of claim 18, wherein the attachment means that attach the shoulder support harness to the upper support beam is comprised of screws, glue-like substances or hook and loop-type fasteners.

20. A method for providing spinal support, alignment, and back muscle assistance when external forces are applied to a user's upper body using the adjustable back support device as claimed in claim 1, said method comprising:

positioning the shoulder support harness atop the shoulders of the user;

positioning the waist support belt around the user's hips;

positioning the upper support beam and the main support beam centrally on the user's back so that they are aligned with the user's spinal column;

adjusting length of the upper support beam and the main support beam to conform to the user's height by positioning a main support beam hinge atop the user's tailbone area, then inserting the upper support beam into the height adjustment assembly of the main support beam to achieve correct positioning, wherein the user is able to determine degree of insertion of the upper beam support into the main support beam by viewing a reference scale shown on the upper support beam;

securing the shoulder support harness on the user by securing the pair of harness straps onto the waist support belt;

adjusting tension of the elastic support strap by rotating the tensioner arm of the elastic support strap tensioner assembly upwardly and placing the tensioner arm into one of a plurality of lockable positions on the tensioner base; and locking the tensioner arm into the one of the plurality of lockable positions with the tensioner arm pin so that the tensioner arm roller is stationary on the elastic support strap and maintains a desired degree of tension in the elastic support strap, wherein when the user bends at the waist and external forces are applied to the user's upper body to cause exertion of the back muscles, the main support beam hinge allows articulation of the main support beam so that spinal support, spinal alignment, and back muscle assistance is provided to the user.

\* \* \* \* \*